US012408921B2

(12) United States Patent
Harrison et al.

(10) Patent No.: US 12,408,921 B2
(45) Date of Patent: Sep. 9, 2025

(54) MAGNETIC POSITIONING/DEPLOYMENT AND RETRIEVAL SYSTEM

(71) Applicant: The Regents of the University of California, Oakland, CA (US)

(72) Inventors: Michael R. Harrison, San Francisco, CA (US); Mohammad Sahlabadi, San Francisco, CA (US); Lauren L. Evans, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 267 days.

(21) Appl. No.: 18/256,903

(22) PCT Filed: Dec. 13, 2021

(86) PCT No.: PCT/US2021/072886
§ 371 (c)(1),
(2) Date: Jun. 9, 2023

(87) PCT Pub. No.: WO2022/133421
PCT Pub. Date: Jun. 23, 2022

(65) Prior Publication Data
US 2024/0023965 A1    Jan. 25, 2024

Related U.S. Application Data

(60) Provisional application No. 63/199,216, filed on Dec. 14, 2020.

(51) Int. Cl.
*A61B 17/11* (2006.01)
*A61B 17/00* (2006.01)

(52) U.S. Cl.
CPC . *A61B 17/1114* (2013.01); *A61B 2017/00876* (2013.01); *A61B 2017/1117* (2013.01)

(58) Field of Classification Search
CPC ...... A61B 17/1114; A61B 2017/00367; A61B 2017/00862; A61B 2017/00876;
(Continued)

(56) References Cited

U.S. PATENT DOCUMENTS 6,126,647 A * 10/2000 Posey ............... A61M 25/0127
600/12
9,339,285 B2    5/2016 Rodriguez-Navarro et al.
(Continued)

OTHER PUBLICATIONS

International Preliminary Report on Patentability dated Jun. 29, 2023, in Application No. PCT/US2021/072886.
(Continued)

*Primary Examiner* — Jocelin C Tanner
(74) *Attorney, Agent, or Firm* — Christian D. Scholz; Weaver Austin Villeneuve & Sampson LLP

(57) ABSTRACT

Apparatuses for placement of magnetic therapeutic devices are provided. Such apparatuses may include an actuation mechanism that includes a movable portion that is movable relative to another portion thereof between at least three different predetermined relative locations, each location associated with a different position of a magnet located within a therapeutic device interface of the apparatus. By moving the magnet between the different locations relative to the therapeutic device interface, different amounts of magnetic clamping force between the magnet and a therapeutic device interfaced with the therapeutic device interface may be developed.

17 Claims, 12 Drawing Sheets

(58) Field of Classification Search
CPC .. A61B 2017/00946; A61B 2017/1117; A61B 2017/1139; A61B 2090/0811
USPC ........................................................ 606/153
See application file for complete search history.

(56) References Cited

U.S. PATENT DOCUMENTS

| | | |
|---|---|---|
| 2010/0168514 A1 | 7/2010 | Callister et al. |
| 2015/0223815 A1 | 8/2015 | Ross et al. |
| 2019/0282272 A1* | 9/2019 | Jenkins ................ A61B 17/221 |
| 2020/0359878 A1 | 11/2020 | Schwarz |

OTHER PUBLICATIONS

International Search Report and Written Opinion dated Mar. 15, 2022, in Application No. PCT/US21/72886.

Zeltser, I., "A Novel Magnetic Anchoring and Guidance System to Facilitate Single Trocar Laparoscopic Nephrectomy," Current Urology Reports, 2008, vol. 9(1), pp. 62-64.

* cited by examiner

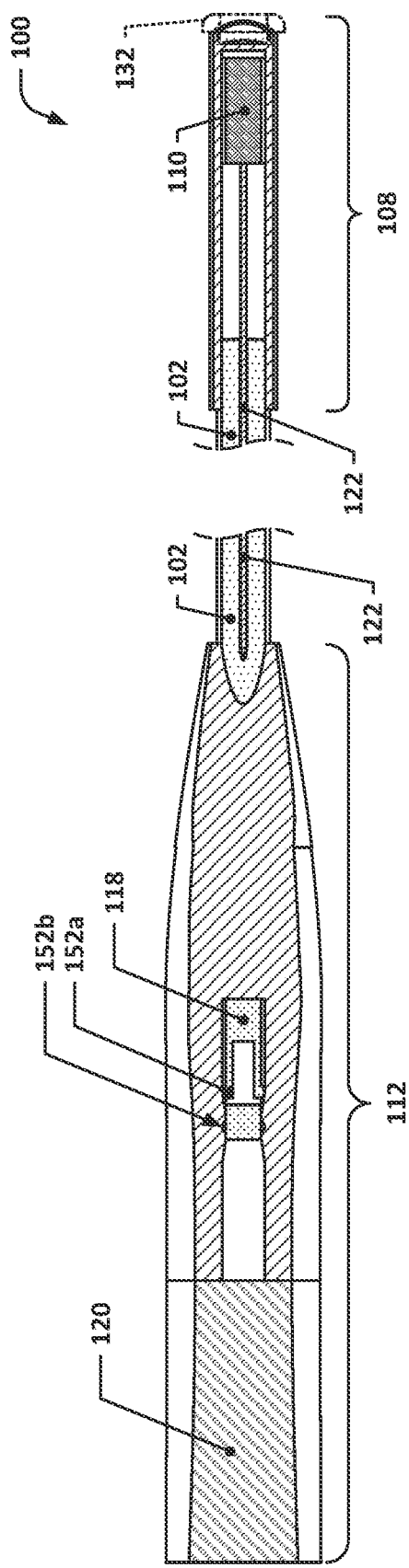
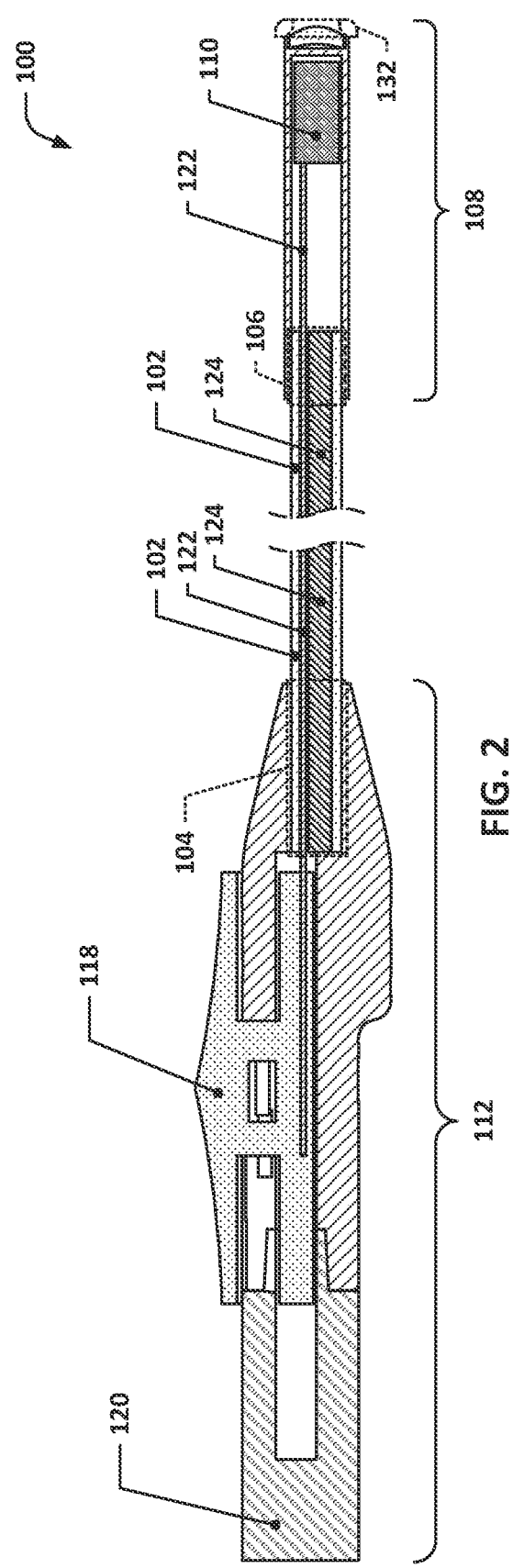

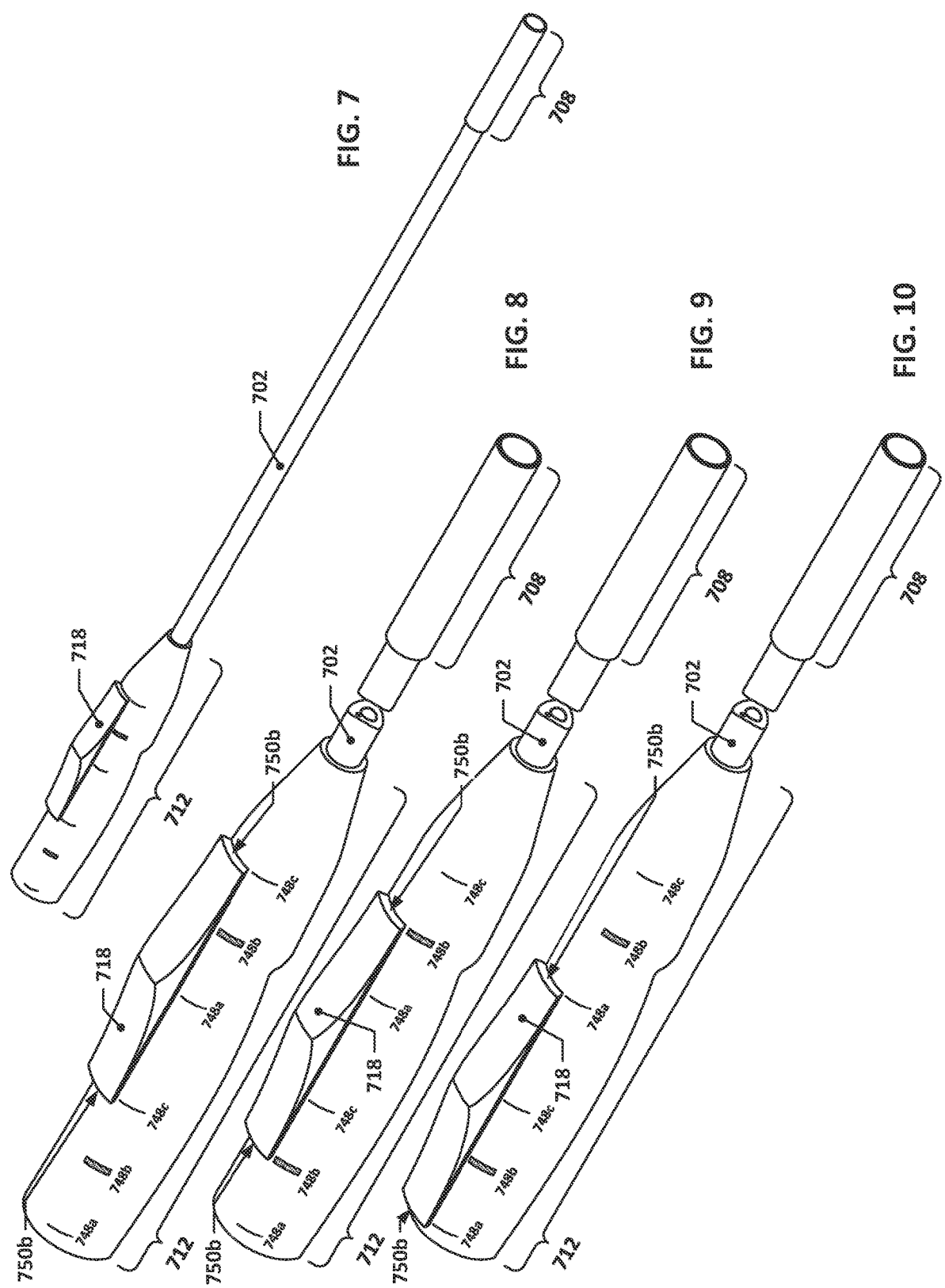

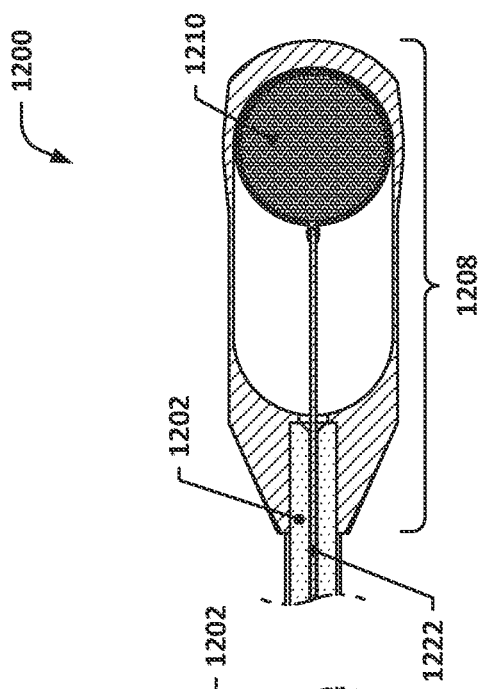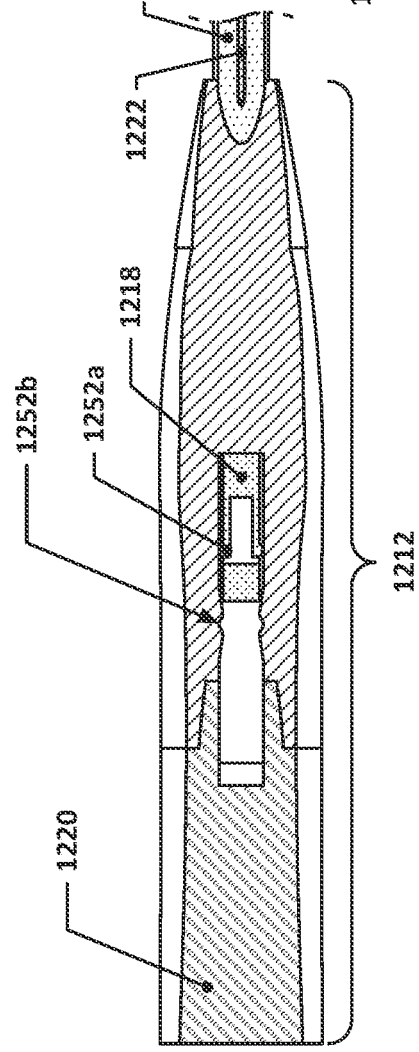
FIG. 12
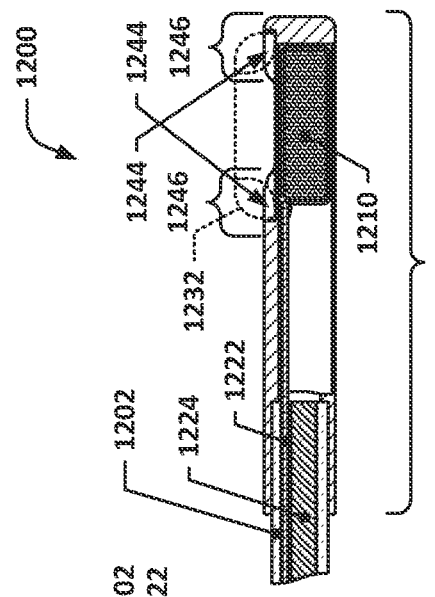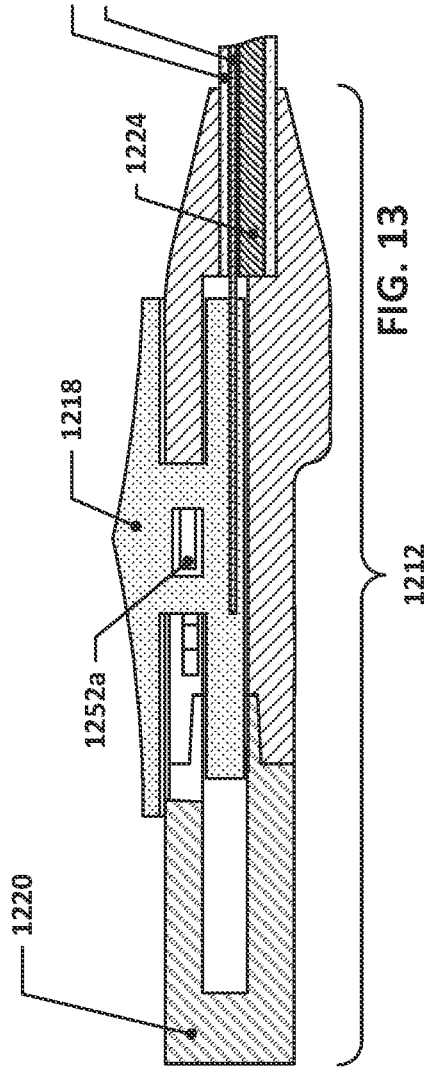
FIG. 13

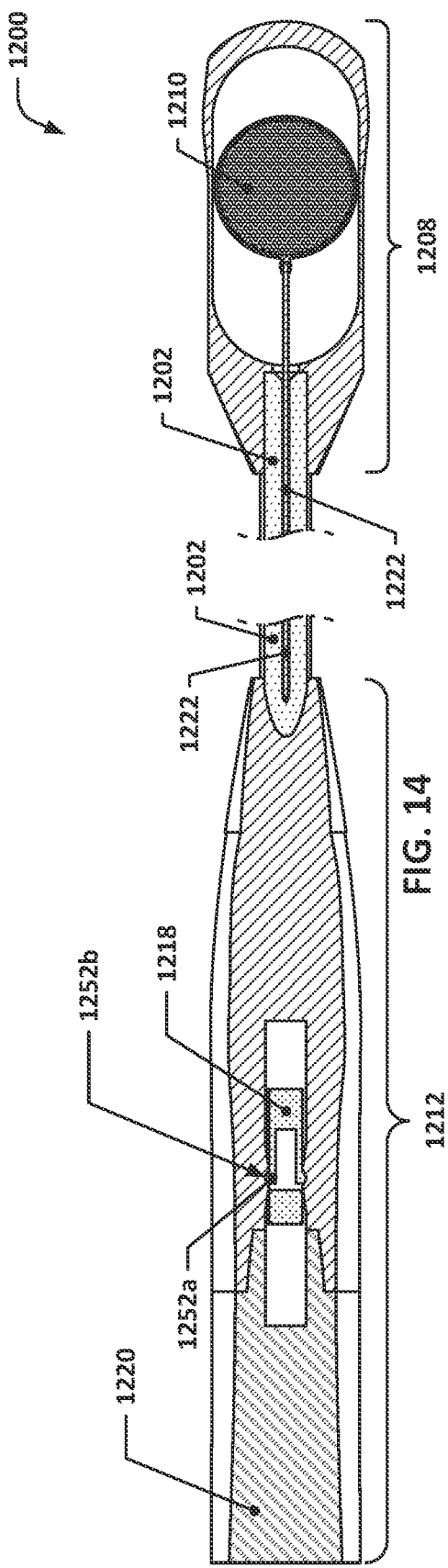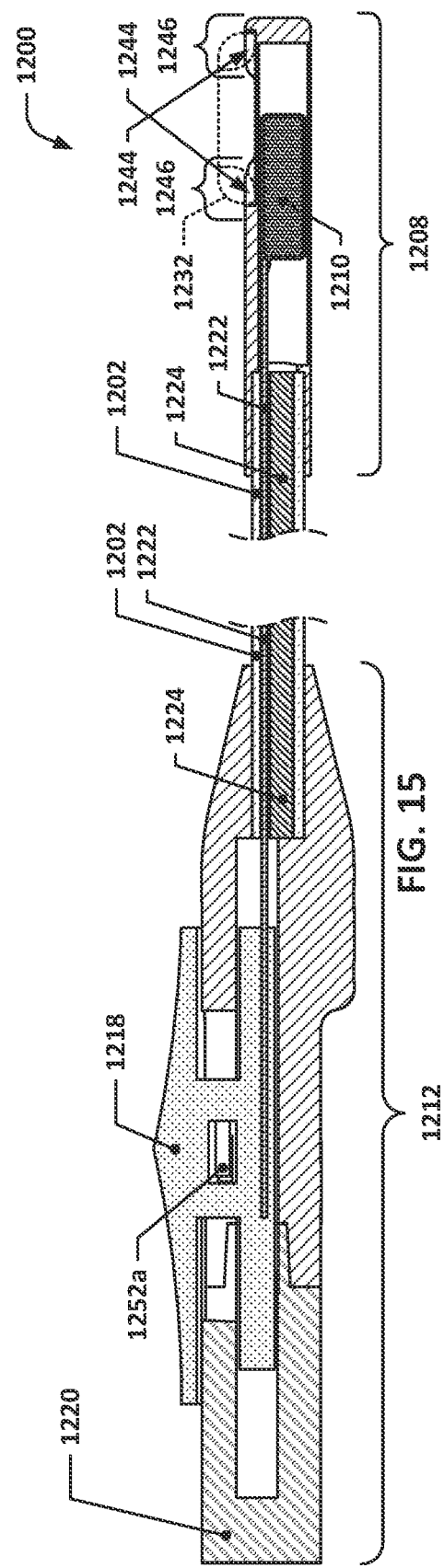

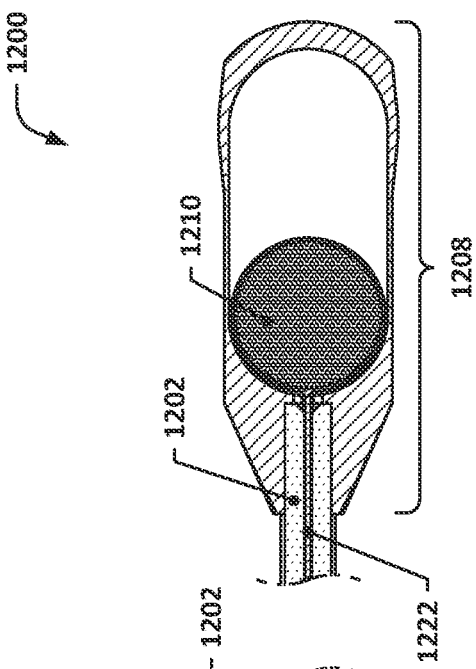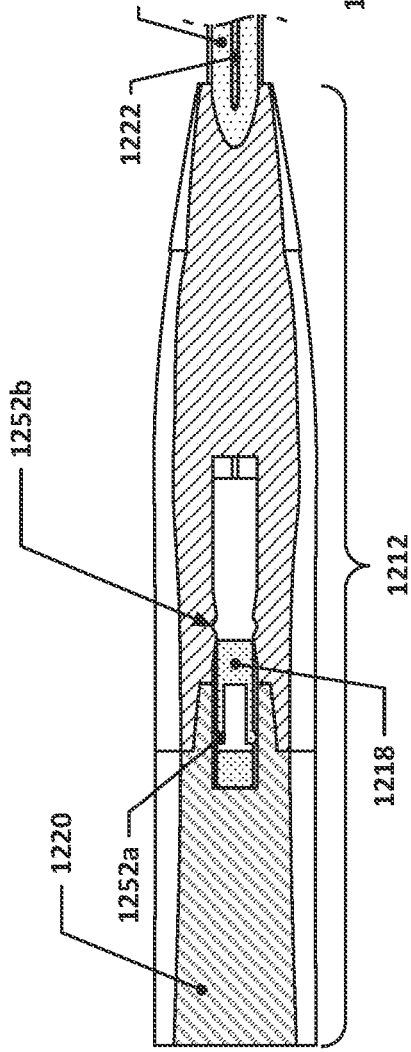
FIG. 16
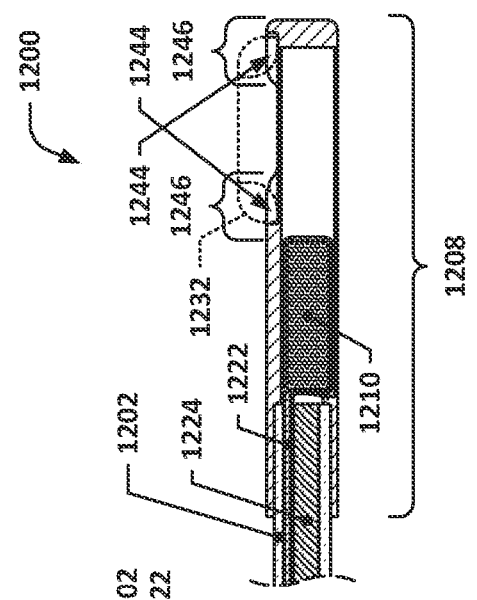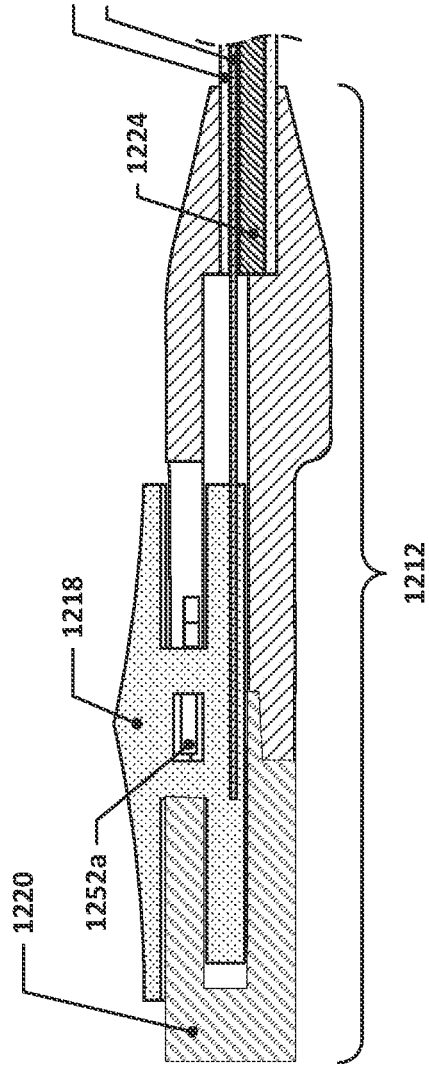
FIG. 17

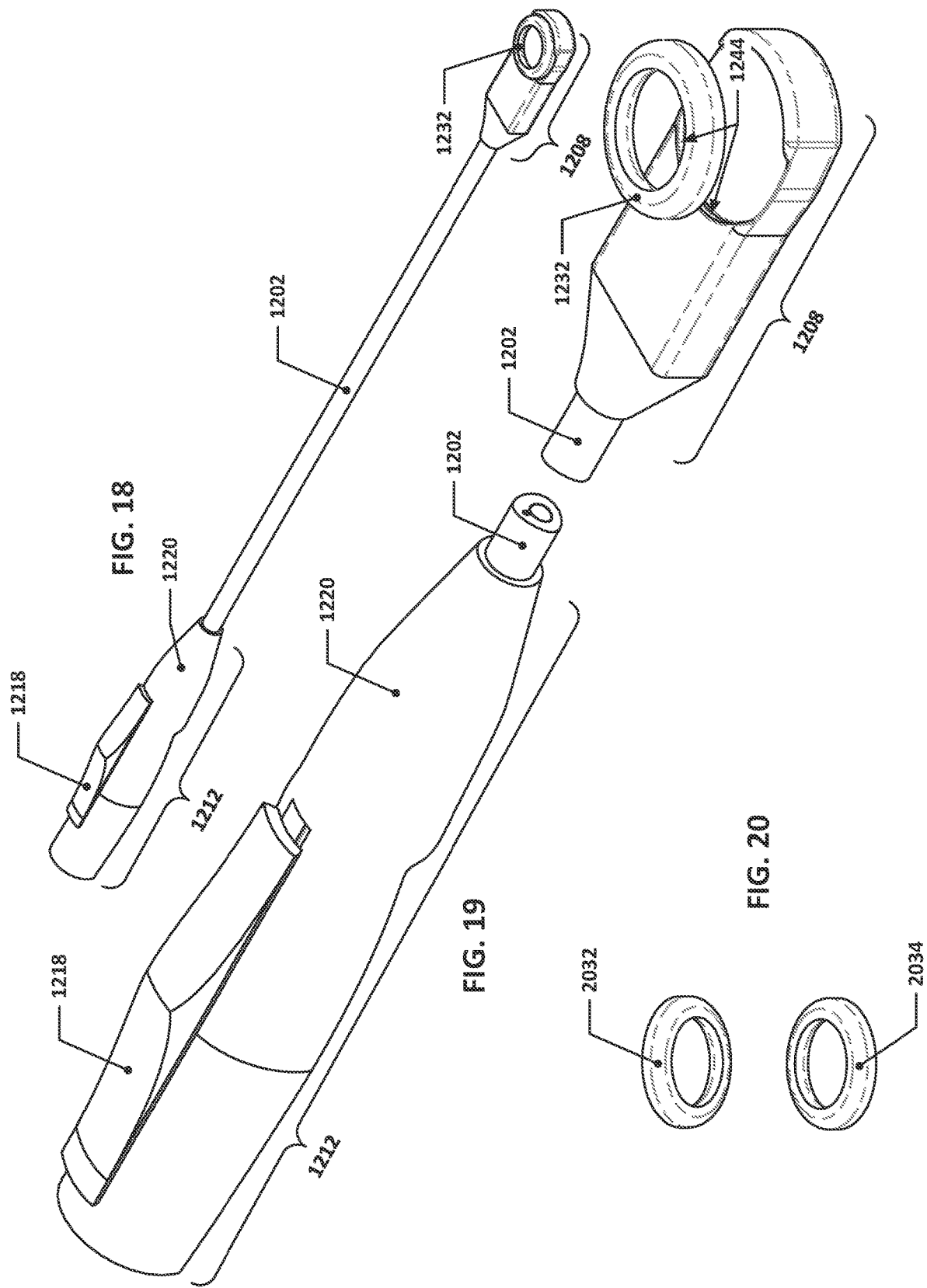

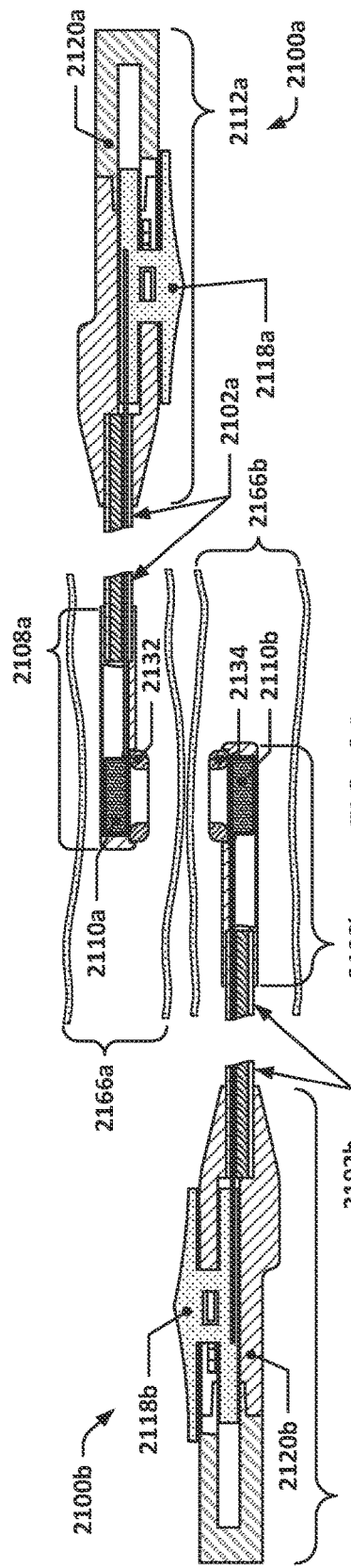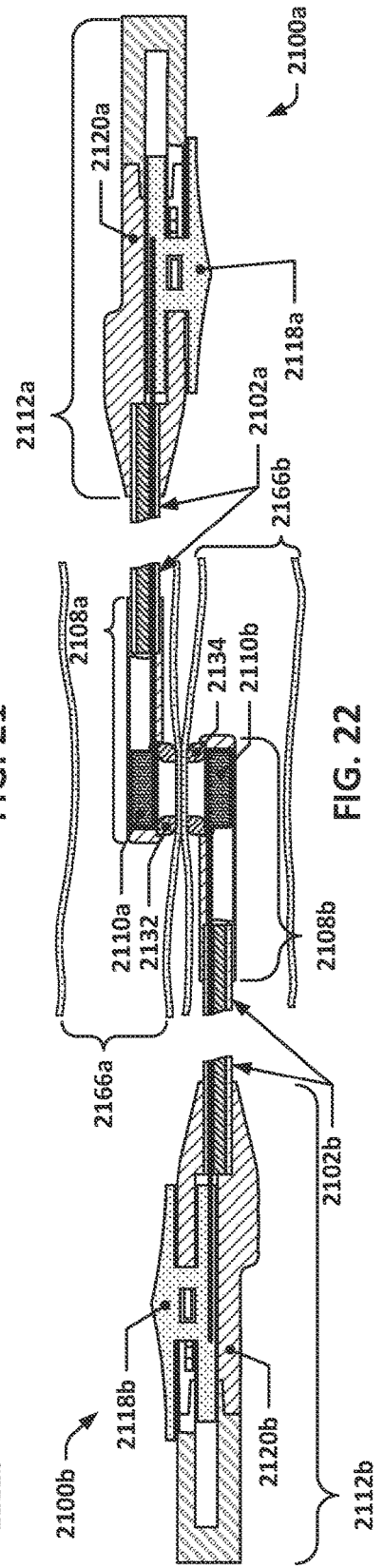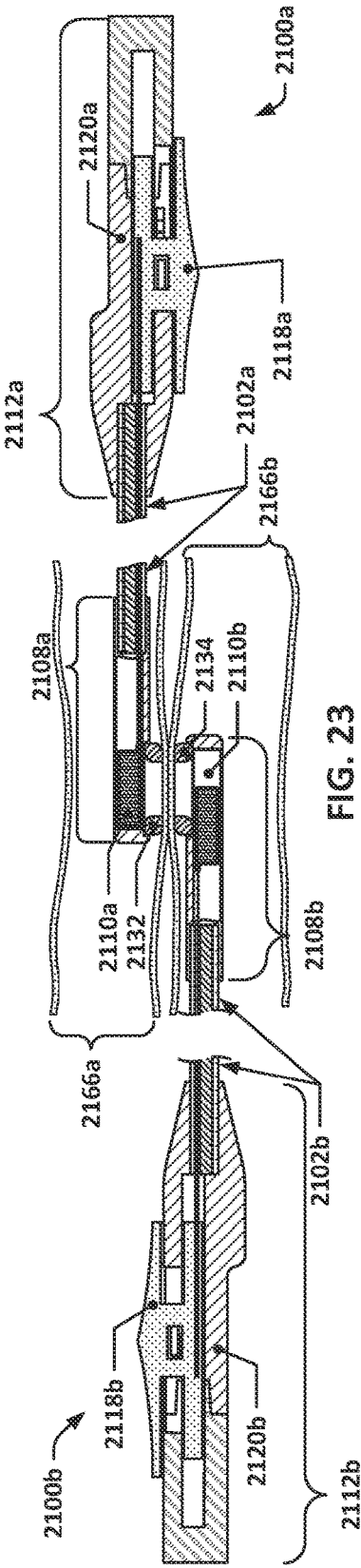

MAGNETIC POSITIONING/DEPLOYMENT AND RETRIEVAL SYSTEM

RELATED APPLICATION

A PCT Request Form is filed concurrently with this specification as part of the present application. Each application that the present application claims benefit of or priority to as identified in the concurrently filed PCT Request Form is incorporated by reference herein in its entirety and for all purposes.

FIELD OF THE INVENTION

This invention relates to devices that may be used to deliver magnetic therapeutic devices to a treatment site in a subject.

BACKGROUND OF THE INVENTION

Some surgical techniques may involve the use of magnetic therapeutic devices, which are devices that may be designed to be implanted in a subject and to magnetically interact with corresponding magnetic therapeutic devices (which may be either internal or external to the subject, depending on the particular type of therapeutic device). Placement of such therapeutic devices in a subject may be challenging, particularly when done endoscopically or laparoscopically.

SUMMARY OF THE INVENTION

The present disclosure includes at least the below-listed implementations, which constitute a non-exhaustive list of potential implementations that may fall within the scope of this disclosure. The present disclosure is not to be limited to only the following listed implementations, and other implementations may be claimed in the context of the disclosure of the disclosure as a whole.

In some implementations, an apparatus may be provided that includes an elongate tubular structure having a first end and a second end, a therapeutic device interface located at the first end thereof, a magnet positioned within the therapeutic device interface, an actuation mechanism connected with the second end of the elongate tubular structure, the actuation mechanism having a first portion that is fixed in space relative to the second end of the elongate tubular structure and a second portion that is movable relative to the second end of the elongate tubular structure, and an actuation member disposed within the elongate tubular structure. In such implementations, the actuation member may connect the magnet to the second portion of the actuation mechanism, and the actuation mechanism may be configured to cause the second portion to be movable, responsive to one or more inputs, between at least a first predetermined location relative to the first portion, a second predetermined location relative to the first portion, and a third predetermined location relative to the first portion. The second predetermined location relative to the first portion may be in between the first predetermined location relative to the first portion and the third predetermined location relative to the first portion, and the actuation member may cause the magnet to move relative to the therapeutic device interface responsive to movement of the second portion of the actuation mechanism relative to the first portion of the actuation mechanism.

In some such implementations, the therapeutic device interface may be configured to support a corresponding first therapeutic device and the first predetermined location relative to the first portion may be selected such that when the second portion is in the first predetermined location relative to the first portion and the corresponding first therapeutic device is interfaced with the therapeutic device interface, the magnet is correspondingly positioned within the therapeutic device interface by the actuation member such that the corresponding first therapeutic device is magnetically mated to the therapeutic device interface by a first magnetic force generated between the magnet and the corresponding first therapeutic device. In such implementations, the second predetermined location relative to the first portion may be selected such that when the second portion is in the second predetermined location relative to the first portion and the corresponding first therapeutic device is interfaced with the therapeutic device interface, the magnet is correspondingly positioned within the therapeutic device interface by the actuation member such that the corresponding first therapeutic device is magnetically mated to the therapeutic device interface by a second magnetic force generated between the magnet and the corresponding first therapeutic device. Furthermore, the first magnetic force may be greater than the second magnetic force.

In some such implementations, the third predetermined location relative to the first portion may be selected such that when the second portion is in the third predetermined location relative to the first portion and the corresponding first therapeutic device is interfaced with the therapeutic device interface, the magnet is correspondingly positioned within the therapeutic device interface by the actuation member such that the corresponding first therapeutic device is not magnetically mated to the therapeutic device interface by any magnetic force generated between the magnet and the corresponding first therapeutic device.

In some implementations, the first therapeutic device may be configured to magnetically mate with a second therapeutic device such that a third magnetic force develops between the first therapeutic device and the second therapeutic device. The third magnetic force may be less than a first threshold force, and the first magnetic force may be greater than the first threshold force.

In some such implementations, the first therapeutic device and the second therapeutic device may be matched pair of magnetic devices configured to generate an anastomosis when placed into a predetermined location in a biological organism with tissue sandwiched between them.

In some further such implementations, a kit may be provided with the apparatus, the first therapeutic device, and the second therapeutic device.

In some implementations, the second magnetic force may be less than the first threshold force.

In some implementations, the therapeutic device interface may be connected with the first end of the elongate tubular structure and may be configured to position the corresponding first therapeutic device such that a centerline of the elongate tubular structure passes through the corresponding first therapeutic device when the corresponding first therapeutic device is interfaced with the therapeutic device interface.

In other implementations, the therapeutic device interface may be configured to position the corresponding first therapeutic device such that when the corresponding first therapeutic device is magnetically mated to the therapeutic device interface, the first therapeutic device is offset from, and does not intersect with, a centerline of the elongate tubular structure.

In some such implementations, the therapeutic device interface may include a body that includes an interior volume housing the magnet, may be sized to permit the magnet to slide along a first axis within the interior volume responsive to movement of the actuation member, and may include one or more stop surfaces that define a stop feature that prevents the first therapeutic device from moving a corresponding amount relative to the therapeutic device interface when the first therapeutic device is magnetically mated with the therapeutic device interface and the magnet is moved responsive to movement of the second portion from the first predetermined location relative to the first portion to the second predetermined location relative to the first portion.

In some implementations, the first predetermined location relative to the first portion may be selected so as to position the magnet further from the first end of the elongate tubular structure than the second location relative to the first portion.

In some implementations, the actuation mechanism may include at least one fiducial mark and one or more reference features, the at least one fiducial mark and the one or more reference features may be distributed between the first portion and the second portion such that the one or more reference features move relative to the at least one fiducial mark when the second portion is moved relative to the first portion, and the at least one fiducial mark and the one or more reference features may be positioned such that, for at least the second predetermined location relative to the first portion, at least one fiducial mark of the at least one fiducial mark aligns with at least one of the one or more reference features.

In some implementations, the actuation mechanism may include a plurality of mechanical biasing features, each mechanical biasing feature may correspond with a different one of the first predetermined location relative to the first portion, the second predetermined location relative to the first portion, and the third predetermined location relative to the first portion, the actuation mechanism may be configured to cause the second portion to move relative to the first portion responsive to application of a first amount of force between the first portion and the second portion, and each mechanical biasing feature may be configured to cause the first amount of force to increase when the second portion is in the corresponding one of the first predetermined location relative to the first portion, the second predetermined location relative to the first portion, and the third predetermined location relative to the first portion as compared locations at least immediately adjacent thereto.

In some implementations, the actuation mechanism may include a controller, an actuator, and one or more position sensors, and the controller may be configured to cause the actuator to controllably move the second portion relative to the first portion to each of the first predetermined location relative to the first portion, the second predetermined location relative to the first portion, and the third predetermined location relative to the first portion responsive to one or more input signals and feedback from the one or more position sensors.

In some implementations, the apparatus may be preconfigured to be used with a first therapeutic device, the first therapeutic device may be configured to magnetically clamp to a second therapeutic device, the first predetermined location relative to the first portion may be selected such that when the second portion is at the first predetermined location relative to the first portion and the first therapeutic device is located in a first relative position to the first end of the elongate tubular structure, the magnet is positioned such that the first therapeutic device is magnetically clamped to the apparatus with a clamping force that exceeds that generated between the first therapeutic device and the second therapeutic device when the first therapeutic device is clamped to the second therapeutic device, and the second predetermined location relative to the first portion may be selected such that when the second portion is at the second predetermined location relative to the first portion and the first therapeutic device is located in the first relative position to the first end of the elongate tubular structure, the magnet is positioned such that the first therapeutic device is magnetically clamped to the apparatus with a clamping force that is less than that generated between the first therapeutic device and the second therapeutic device when the first therapeutic device is clamped to the second therapeutic device.

In some implementations, the elongate tubular structure may be made of a flexible material, and in some such implementations, the apparatus may further include a malleable core that extends through the elongate tubular structure.

BRIEF DESCRIPTION OF THE FIGURES

The following Figures are provided to facilitate understanding of the concepts discussed in this disclosure, and are intended to be illustrative of some implementations that fall within the scope of this disclosure, but are not intended to be limiting—implementations consistent with this disclosure and which are not depicted in the Figures are still considered to be within the scope of this disclosure.

FIG. 1 depicts a top, non-planar section view of an example apparatus according to the present disclosure and in a first state.

FIG. 2 depicts a side section view of the example apparatus of FIG. 1.

FIG. 7 depicts an isometric view of an example apparatus having fiducial marks according to the present disclosure.

FIGS. 8-10 depict isometric broken views of the apparatus of FIG. 7 in three different actuation states.

FIG. 12 depicts a top, non-planar section view of an example apparatus according to the present disclosure and in a first state.

FIG. 13 depicts a side section view of the example apparatus of FIG. 12.

FIG. 14 depicts a top, non-planar section view of the example apparatus of FIG. 12 but in a second state.

FIG. 15 depicts a side section view of the example apparatus of FIG. 14.

FIG. 16 depicts a top, non-planar section view of the example apparatus of FIG. 12 but in a third state.

FIG. 17 depicts a side section view of the example apparatus of FIG. 16.

FIG. 18 depicts an isometric view of the example apparatus of FIG. 12 with a therapeutic device mounted to the therapeutic device interface.

FIG. 19 is a broken isometric view showing the apparatus of FIG. 18 with the therapeutic device lifted off of the therapeutic device interface.

FIG. 20 is an isometric view of a pair of therapeutic devices pulled away from each other at an angle.

FIGS. 21-28 depict various stages of therapeutic device installation using apparatuses such as are disclosed herein.

DETAILED DESCRIPTION

Figure 3:
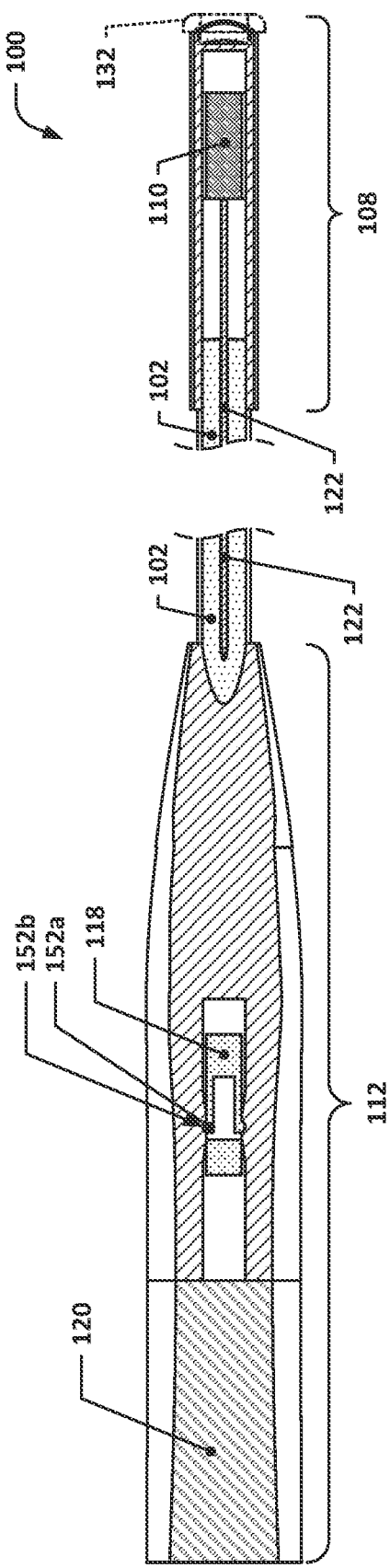
FIG. 3 depicts a top, non-planar section view of the example apparatus of FIG. 1 but in a second state.

Certain surgical procedures may involve the use of magnetic therapeutic devices, i.e., therapeutic devices that either incorporate magnets or that include a material that is able to be magnetically attracted by a magnet. Some particular examples of such magnetic therapeutic devices are matched pairs of annular magnets that may each be positioned within a different lumen, or different portions of the same lumen, of an organism in order to magnetically clamp the tissue walls defining the lumens or portions of a lumen together. When properly sized and installed, such matched pairs of annular magnets may cause the tissue around the outer perimeter of the clamped zone to fuse together while causing the clamped tissue and the tissue in the interior of the annular magnets to necrose, eventually causing the clamped tissue to break free of the fused tissue, thereby creating an anastomosis.

For example, there are several structures in organisms or human bodies that are amenable to creating an anastomosis in this way. These include, but are not limited to, the esophagus, the small bowel, the colon, the biliary tree, and the urinary tract. One such specific example in which such therapeutic devices may be used is the treatment of the pathology of esophageal atresia. Esophageal atresia is a congenital malformation in which a neonate is born with their esophagus in two non-communicating pouches. In this case, one of the paired annular magnets is placed in the upper esophageal pouch and one in the lower esophageal pouch. The pair of annular magnets are then mated with the esophageal tissue clamped between them. As described above, this then facilitates the formation of an esophageal anastomosis which establishes esophageal continuity thereby repairing the malformation of esophageal atresia.

In the biliary tree, the main duct draining the liver and the pancreas to the small intestine can stricture. The etiology of stricture is multifactorial and includes but is not limited to prior surgical operations, trauma, inflammatory disease and recurrent infection. The stricture, or narrowing of the main drainage duct, causes insufficient drainage of the bile and pancreatic enzymes produced by the liver and pancreas, respectively. Without adequate drainage, the bile and pancreatic enzymes back-up into the liver and pancreas, which results in significant inflammation of the affected organs and systemic illness. This requires placement of an external drainage tube through the abdominal wall into the biliary tree to allow for decompression of the biliary system and relieve the inflammation due to the congestion of the liver and pancreas, caused by the backup of bile and pancreatic enzymes in the ductal system. In this case, the paired annular magnets may be delivered into the biliary tree with one on either side of the stricture. The magnets are then mated with the diseased, strictured tissue clamped between them. This removes the strictured segment of the duct by facilitating formation of a new anastomosis of the bile duct that is healthy and not narrowed. The removal of the narrowed stricture allows the physiologic drainage of the biliary tree to be restored and the external drainage tube to be removed.

Strictures can also affect the urinary tract. One such example is a stricture that forms in the ureter, the tube that drains urine produced by the kidney into the bladder. The etiology of stricture of the ureter is multifactorial and includes but is not limited to kidney stones, surgical operations, trauma, inflammatory disease and recurrent infections. In similar fashion to the biliary tree, the narrowing caused by the stricture results in insufficient drainage of the kidney causing congestion and inflammation due to the backup of urine in the kidney. This requires placement of an external drainage tube inserted through the flank into the central portion of the kidney, the renal pelvis, to facilitate external drainage of the urine and decompression of the kidney. As with the biliary case discussed above, the paired annular magnets are delivered into the ureter with one on either side of the stricture. One annular magnet is delivered through the external drainage tube through the flank into the ureter and the other is delivered to the ureter through the urethra and bladder. The magnets are then mated with the diseased, strictured tissue clamped between them. This removes the strictured segment of the ureter and facilitates formation of a new anastomosis of the ureter that is healthy and not narrowed. The removal of the narrowed stricture allows the physiologic drainage of the ureter to be restored and the external drainage tube through the flank to be removed.

In the small bowel and colon, surgical operations frequently require creation of an anastomosis between two segments of bowel that are not normally directly opposed to one another to establish continuity between the two segments of bowel. Need to create a new connection between two segments of bowel includes but is not limited to need to remove an interposing segment of bowel, trauma resulting in bowel injury, and surgical reconfiguration of the bowel anatomy for the treatment of diseases, such as metabolic syndrome and obesity. The paired annular magnets are delivered into the lumens of the two segments of bowel between which an anastomosis is desire. In the position of the desired anastomosis, the two annular magnets are mated together with one wall of each segment of bowel interposed between them. The compression of the tissue between the paired, mated annular magnets results in the gradual formation of an anastomosis, which establishes the desired continuity between the two segments of bowel.

It will be understood that the techniques and apparatuses/systems discussed herein may be used in the context of such treatments, as well as in other treatments not discussed herein but that may use one or more magnetic therapeutic devices.

The present inventors realized that placing, orienting, and installing such magnetic therapeutic devices may be facilitated through the use of an apparatus that is able to be transitioned between at least three different modes of operation through the operation of an actuation mechanism that causes the location of a magnet proximate to where the apparatus supports a magnetic therapeutic device to move between at least three corresponding locations relative to the magnetic therapeutic device.

In one such location, the magnet may be positioned proximate to where the magnetic therapeutic device is supported by the apparatus, thereby magnetically clamping the magnetic therapeutic device to the apparatus. In another such location, the magnet may be positioned in a location that causes the magnetic clamping of the magnetic therapeutic device provided by the magnet in the first location to effectively be neutralized, thereby causing the magnetic clamping of the magnetic therapeutic device to no longer be in effect and allowing the magnetic therapeutic device to simply fall off of the apparatus when appropriately positioned. In yet a third such location, the magnet may be moved to a location in between the other two locations. In this third location, the magnetic therapeutic device may still be clamped to the apparatus by the magnet, but with a lower amount of clamping force than in the first location discussed above.

The third location may be selected so as to produce a generally known amount of clamping force on the magnetic therapeutic device that is calibrated to cause the magnetic therapeutic device to remain clamped to the apparatus during positioning and installation but be pulled free of the apparatus by a greater magnetic force provided by, for example, another magnetic therapeutic device that is positioned in a similar manner at the installation site. In other words, when two magnetic therapeutic devices are properly installed, the magnetic force clamping them together will be stronger than the magnetic clamping force provided by the apparatus. In particular, it will be understood that proper installation of two matched magnetic therapeutic devices may require installation in a location where the tissue clamped between the two magnetic therapeutic devices is within a predetermined thickness range, which may, in turn, indirectly govern how much magnetic clamping force develops between the two magnetic therapeutic devices which, in turn, governs what the magnetic clamping force between the apparatus and the magnetic therapeutic device should be in the third location. In some implementations, the third location may be selected such that the magnetic force that clamps the magnetic therapeutic device to the apparatus is sufficient to keep the therapeutic device in place on the apparatus during placement but allows the therapeutic device to be easily pulled free of the apparatus once the therapeutic device is installed in a subject—without potentially causing injury to the subject. For example, the third location may be selected such that the magnetic force that clamps the magnetic therapeutic device to the apparatus is sufficiently low that transferring such force to the subject's tissue walls at the location where the therapeutic device is installed does not cause injury to the subject, e.g., tearing of the tissue. By way of further example, the third location (and resulting magnetic clamping force between the apparatus and the therapeutic device) may be selected such that the therapeutic device may, once clamped in place at the treatment site by a second therapeutic device, be able to be disengaged from the apparatus merely by lightly jiggling the apparatus.

Generally speaking, the apparatus may be designed to allow the user to reliably operate the apparatus so as to be able to move the magnet between at least the three predetermined locations discussed above with a high degree of certainty. Being able to operate the apparatus to place the magnet in the intermediate predetermined location is particularly important since if the magnet is too close to the magnetic therapeutic device being clamped, the magnetic clamping force may overcome any potential magnetic clamping force between the magnetic therapeutic device and the other magnetic therapeutic device to which it is clamped, thereby causing the magnetic therapeutic devices to become separated when the apparatus is pulled away. Similarly, if the magnet is too far away from the magnetic therapeutic device, the clamping force may be insufficient to clamp the magnetic therapeutic device in place during positioning and it may prematurely pull away from the apparatus and clamp to the other magnetic therapeutic device but potentially in the wrong location within the patient.

Such apparatuses are markedly distinct from "binary" devices in which a magnet may be moved between two locations and any location therebetween, but in which the magnet may only be moved with certainty by the user to either of the two "end" locations. In such binary devices, movement of the magnet to a particular position in between the end locations with any certainty is generally not possible by a human operator since such devices are not configured to give feedback to the user as to whether the magnet (or at least the actuation mechanism that causes the magnet to move) is in the correct intermediate location.

FIG. 1 depicts a top, non-planar section view of an example apparatus according to the present disclosure and in a first state. FIG. 2 depicts a side section view of the example apparatus of FIG. 1. As can be seen in FIGS. 1 and 2, an apparatus 100 is shown that features an actuation mechanism 112 coupled to a therapeutic device interface 108 by an elongate tubular structure 102. The elongate tubular structure 102 may have one or more holes or passages extending along the length thereof to allow another component or components to be placed within the elongate tubular structure 102. In the depicted example, the elongate tubular structure 102 has two passages that extend through the length of the elongate tubular structure 102—a larger-diameter passage that has a stylet 124 or other structure extending therethrough, and a smaller-diameter passage that has an actuation member 122 extending therethrough. In other implementations, however, there may be additional or fewer such passages. For example, in some implementations, there may be only a center passage, with the actuation member disposed therein. In other implementations, there may be passages provided for fiber optic elements that may be used to provide for light transmission through the elongate tubular structure, e.g., to provide for the ability to obtain images of the treatment site via a fiberoptic borescope, for example, and/or provide illumination of the treatment site via a fiberoptic lightguide coupled to a light source.

In some implementations, the elongate tubular structure 102 may be made of a flexible material and have a length selected to facilitate insertion into, and navigation through, any of a variety of anatomical passages in which magnetic therapeutic devices may be installed. For example, such lengths may range between about 7 and 100 inches. Such flexible arrangements may be used for endoscopic surgical procedures, allowing for magnetic therapeutic devices to be delivered and placed endoscopically. In other implementations, the elongate tubular structure 102 may be made of a rigid or semi-rigid material, allowing for some minor deflection, and generally be of a shorter length, e.g., between 5 and 15 inches in length. Such rigid or semi-rigid implementations may be more well-suited for applications in which the magnetic therapeutic devices are delivered laparoscopically.

The stylet 124, if used, may be made of a malleable material that is easily shaped by hand but is also sufficiently rigid enough to maintain its shape during use. This may allow the elongate tubular structure 102 to be formed into particular shapes that allow it to be navigated through some anatomical passages. The actuation member 122 may generally be made from a material that is flexible but strong enough to avoid buckling in any unconstrained areas when subjected to a compressive load along its axis.

The actuation mechanism 112 may have a first portion 114 and a second portion 116 that is movable relative to the first portion 114 responsive to receipt of one or more inputs by elements of the actuation mechanism 112. In some implementations, such as that shown in FIGS. 1-6, the actuation mechanism 112 may be manually operable, e.g., being designed to receive input from manual interaction between a human operator and portions of the actuation mechanism 112. In other implementations, however, the actuation mechanism may be an electromechanical mechanism and receive electrical signals as input that causes the actuation mechanism to operate.

In the implementation of FIG. 112, the first portion 114 of the actuation mechanism 112 comprises a handle 120 that includes an internal passage and connects with a first end 104 of the elongate tubular structure 102. The second portion 116, in contrast, includes an internal portion that is housed within the internal passage of the first portion 114 and an external portion that is external to the first portion 114. For example, the second portion 116 may be provided by a slider 118 that can be translated relative to the first portion 114/handle 120, with the internal portion sliding within the internal passage of the handle 120 while the external portion is physically accessible to users on the outside of the handle 120. The handle 120 may have a channel or elongate opening in it that allows a bridging portion of the slider 118 to span between the internal and external portions of the slider 118 to connect them together.

The second portion 116 may be connected with the actuation member 122 such that when the second portion 116 is moved relative to the first portion 114, the actuation member 122 experiences similar relative movement, which is translated through the elongate tubular structure 102 along the length of the actuation member 122 that extends therethrough.

The elongate tubular structure 102 may be connected at a second end 106 to the therapeutic device interface 108, which may contain a magnet 110 that is connected to the actuation member 122. The therapeutic device interface 108 may have an internal volume or cavity that is sized and shaped to allow the magnet 110 to translate within the therapeutic device interface 108 in response to movement of the actuation member 122 that is connected to the magnet 110. Thus, the actuation member 122 may serve to transmit translational motion inputs from the actuation mechanism 112 to the magnet 110. For example, sliding the slider 118 towards the elongate tubular structure 102 relative to the handle 120 may cause the magnet 110 to move towards the end of the therapeutic device interface 108 furthest from the elongate tubular structure 102. Similarly, sliding the slider 118 away from the elongate tubular structure 102 relative to the handle 120 may cause the magnet 110 to move away from the end of the therapeutic device interface 108 furthest from the elongate tubular structure 102 (which may be referred to herein as the distal end of the therapeutic device interface).

As shown in FIG. 1, the slider 118/second portion 116 is positioned in a first predetermined location relative to the handle 120/first portion 114 that is, in this example, determined by the length of the slot in which the bridging portion of the slider 118 is located. As can be seen, the bridging portion of the slider 118 has bottomed out/butted up against one end of the slot in the handle 120, thereby preventing further movement of the slider 118 towards the elongate tubular structure 102. When the slider 118, e.g., the second portion 116, is positioned in the first predetermined location, the magnet 110 is generally positioned at the closest it can be to the distal end of the therapeutic device interface 108.

The distance between the magnet 110 and the distal end of the therapeutic device interface 108 may be selected such that the magnetic force that may develop between the magnet 110 and a particular magnetic therapeutic device or range of magnetic therapeutic devices (which may also simply be referred to herein as a "therapeutic device" or "therapeutic devices") that may be positioned at the distal end of the therapeutic device interface 108, e.g., as shown by the dotted outline of an example therapeutic device 132, is sufficient to magnetically mate the therapeutic device 132 to the therapeutic device interface 108.

As used herein, the phrase "magnetically mated," e.g., such as in "a first component is magnetically mated to a second component or structure," refers to a condition in which the first component is held in place relative to the second component or structure by virtue of a magnetic attractive force that is sufficiently strong enough to retain the first component in position relative to the second component regardless of orientation of the first component and second component relative to the Earth's gravitational field. In other words, the magnetic force is strong enough, by itself, to overcome the gravitational force that acts on the first component.

As will be evident, when the slider 118 is moved towards the elongate tubular structure 102, the magnet 110 will similarly move towards the distal end of the therapeutic device interface 108 by a generally corresponding amount (depending on how far from the centerline of the elongate tubular structure 102 the centerline of the actuation member 122 is, there may be some variation in how much the magnet 110 moves relative to the therapeutic device interface 108 as compared to how much movement the second portion 116 experiences relative to the first portion 114 if such movement occurs while the elongate tubular structure is flexed into a non-straight shape).

As can be seen, the slider 118 and the handle 120 in this example include a mechanical stop feature that includes elements 152a and 152b. Mechanical stop element 152a takes the form of a flexible, cantilevered beam spring with an outward-facing bump or protrusion that may releasably engage with a notch or other similar recessed feature/element 152b that is located so that the bump or protrusion on the mechanical stop element 152 engages with the notch or similar feature when the slider 118 is in a particular location relative to the handle 120. As shown in FIGS. 1 and 2, the slider 118 includes opposing elements 152a and handle 120 includes opposing elements 152b, but it will be understood that the locations of these elements may be reversed in other implementations, with elements 152a located on the handle and elements 152b located on the slider.

It will be further understood that such elements may be generally described as mechanical biasing features that may act to increase the amount of force that is needed to cause the second portion 116 to slide or translate relative to the first portion 114 when the second portion 116 is in a particular position relative to the first portion 114 associated with such a mechanical biasing feature as compared to the force required to effect similar such movement in relative positions between the first portion 114 and the second portion 116 that are not associated with such mechanical biasing features. Other examples of such mechanical biasing features include spring-loaded detent mechanisms, pairs of magnetic members that may be configured to reach peak magnetic attraction force when in a particular position relative to each other, a spring-loaded or electromechanical catch that locks the second portion 116 in place when in a particular location relative to the first portion 114 (and which may then be released, e.g., through depressing a button or other release device), etc.

Figure 4:
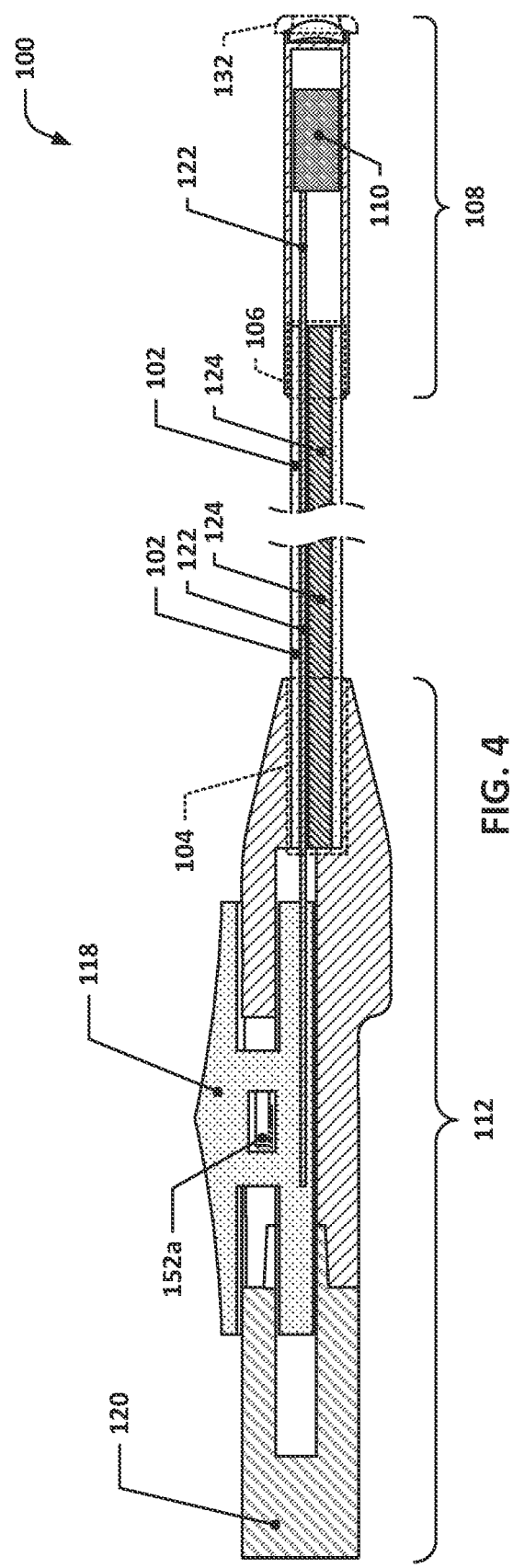
FIG. 4 depicts a side section view of the example apparatus of FIG. 3.

FIG. 3 depicts a top, non-planar section view of the example apparatus of FIG. 1 but in a second state, e.g., a state that corresponds with the position of the second portion 116 relative to the first portion when the elements 152a and 152b are engaged with one another. FIG. 4 depicts a side section view of the example apparatus of FIG. 3.

In the configuration of FIG. 3, the second portion 116 has been moved to a second predetermined location relative to the first portion 114. The second location relative to the first portion 114 is predetermined because it is a position in which the mechanical biasing features discussed above are engaged, thereby increasing the actuation force needed to actuate the actuation mechanism 112 further.

As used herein, a mechanism that is configured to cause a portion thereof to be movable between multiple predetermined locations relative to another portion thereof is a device that has features that allow or is otherwise designed to allow the movable portion to be reliably positioned in any of those predetermined locations with little or no uncertainty by a user of the mechanism. For example, as with the above-discussed apparatus, the mechanism may have one or more spring-loaded detents on one or both of the movable portion and the other portion that may engage with one or more corresponding features on the other of the movable portion and the other portion when in each of the predetermined locations, thereby providing an increased resistance against further relative movement between the two portions when the movable portion is in each of the predetermined locations relative to the other portion as compared to when the movable portion is not in one of the predetermined locations relative to the other portion. In another example, the mechanism may have multiple fiducial marks on one and/or both of the movable portion and the other portion that may align with a corresponding mark on the other of the movable portion and the other portion when the movable portion is in a corresponding one of the predetermined locations. In yet another example, the mechanism may be an electromechanical mechanism that includes one or more actuators, one or more position sensors, and a controller that can be caused to control the one or more actuators to cause the movable portion to move relative to the other portion and, based on feedback from the one or more position sensors, cause the one or more actuators to stop moving the movable portion when the movable portion is in any of the predetermined locations relative to the other portion.

It will be understood that any mechanism that allows for movement of one portion thereof relative to another portion thereof can admittedly be said to allow the movable portion to be positioned at any location within the range of movement permitted—however, such a device cannot be said to be configured to cause the movable portion to be movable to a predetermined location within that range of movement locations unless the mechanism includes some feature or features, as discussed above, that permit the user to reliably position the movable portion in that predetermined location. The predetermined location, in other words, represents a location that the mechanism is designed to preferably cause the movable portion to stop at during movement or to allow a user to recognize that the movable portion is in the predetermined location during actuation of the mechanism.

As shown in FIGS. 3 and 4, when the second portion 116 is in the second predetermined location relative to the first portion 114, the magnet 110 is moved further form the distal end of the therapeutic device interface 108 than when the second portion 116 is in the first predetermined location relative to the first portion 114. This causes the magnetic attractive force between the magnet 110 and the therapeutic device 132 to correspondingly decrease, although the second predetermined location may be selected such that the magnetic attractive force between the magnet 110 and the therapeutic device 132 is still sufficiently strong enough to magnetically mate the therapeutic device 132 to the therapeutic device interface 108. As discussed above, the second predetermined location relative to the first portion may be selected so as to generate a particular amount of magnetic force that may generally hold the therapeutic device 132 in place relative to the therapeutic device interface 108 while otherwise permitting the therapeutic device 132 to be pulled free of the therapeutic device interface when magnetically clamped to a corresponding therapeutic device under the boundary conditions associated with proper installation of the therapeutic devices. In contrast, when the second portion 116 is in the first predetermined location relative to the first portion 114, the magnetic clamping force that magnetically mates the therapeutic device 132 to the therapeutic device interface 108 is strong enough to pull the therapeutic device 132 away from the other therapeutic device 132 to which it is magnetically mated (assuming that the other therapeutic device 132 is otherwise held in place).

Figure 5:
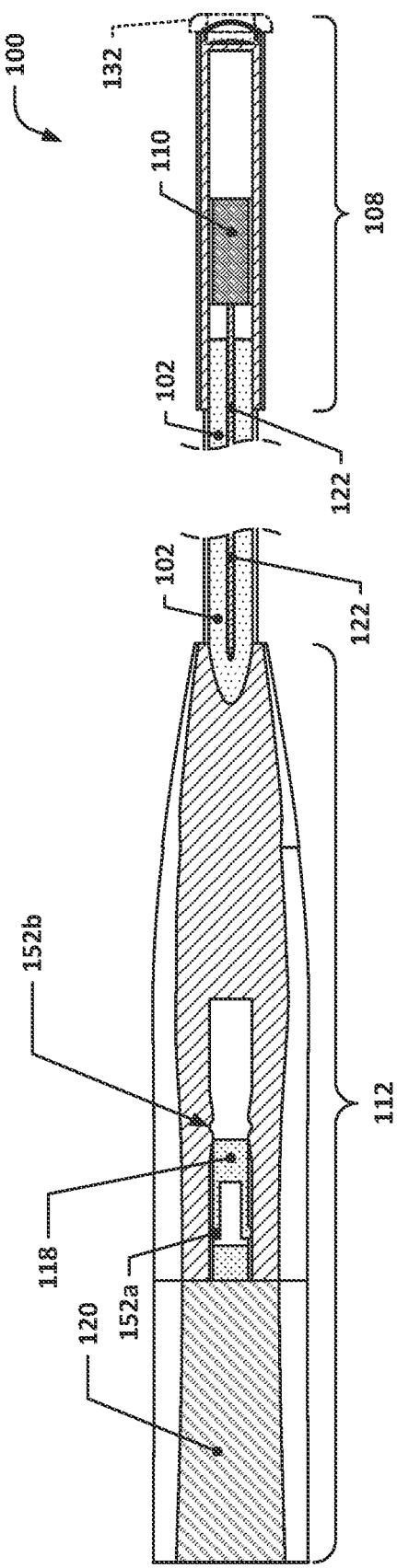
FIG. 5 depicts a top, non-planar section view of the example apparatus of FIG. 1 but in a third state.
Figure 6:
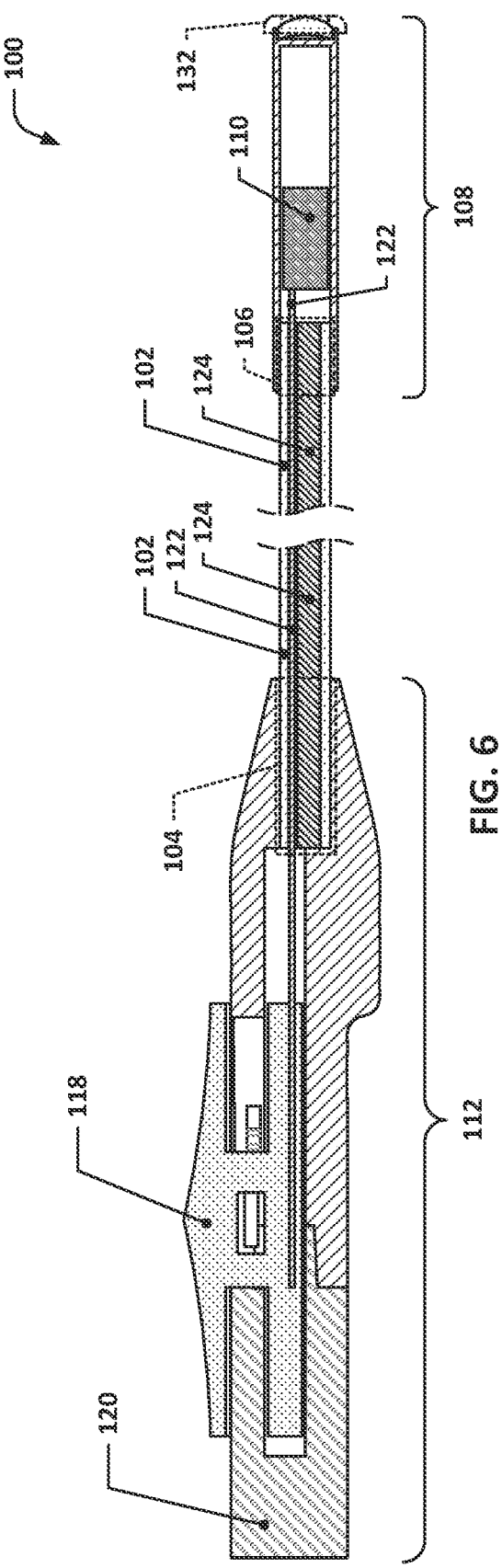
FIG. 6 depicts a side section view of the example apparatus of FIG. 5.

In addition to the first predetermined location and the second predetermined location, the apparatus 100 may also be configured to permit the second portion 116 to be moved to a third predetermined location relative to the first portion 114. FIG. 5 depicts a top, non-planar section view of the example apparatus of FIG. 1 but in a third state that corresponds with the second portion 116 being in the third predetermined location relative to the first portion 114. FIG. 6 depicts a side section view of the example apparatus of FIG. 5.

As can be seen, the third predetermined location is similar to the first predetermined location but represents the opposite extreme with regard to the relative positioning between the first portion 114 and the second portion 116. Thus, when the second portion 116 is in the third predetermined location relative to the first portion 114, the magnet 110 is generally in a location furthest from the distal end of the therapeutic device interface 108 (at least, within the range of movement permitted by the apparatus 100). When the second portion 116 is in the third predetermined location relative to the first portion 114, the magnet 110 is sufficiently far enough from the therapeutic device interface 108 to no longer cause the therapeutic device 132 to be magnetically clamped or clampable to the therapeutic device interface 108, thereby allowing the therapeutic device 132 to be released from the apparatus 100.

In the example above, the movement of the second portion 116 relative to the first portion 114 is able to be precisely controlled by the user to allow the second portion 116 to be moved to the first predetermined location relative to the first portion 114, the second predetermined location relative to the first portion 114, and the third predetermined location relative to the first portion 114. In the case of the second predetermined location relative to the first portion 114, the mechanical biasing provided by the elements 152a and 152b of the mechanical stop provides tactile feedback to the user when the second portion 116 is in the second predetermined location relative to the first portion 114, thereby allowing for precise positioning of the second portion 116 at the first predetermined location. In the case of the first and third predetermined locations relative to the first portion 114, the bottoming out of the bridging portion of the slider 118 at either end of the slot of the handle 120. This similarly allows the second portion 116 to be positioned by the user with certainty at either the first predetermined location or the third predetermined location relative to the first portion 114, e.g., by pushing the slider 118 in either direction until it can no longer be pushed further.

It will be further appreciated that there may be additional predetermined locations that the second portion 116 may be movable to relative to the first portion 114 for a given apparatus, but, at a minimum, there will be at least three such predetermined positions for apparatuses, such as are described herein, that are designed to facilitate proper placement and installation of a therapeutic device.

For example, the first and/or third predetermined position may instead be associated with a corresponding mechanical stop(s) or similar feature(s), thereby allowing for even further movement beyond those locations in one or both directions until the slider 118 bottoms out and is not capable of further movement in a given direction.

As discussed earlier, other implementations may utilize other types of actuation mechanisms, including, for example, implementations where the actuation mechanism itself does not include any devices or components that provide tactile feedback (such as are provided by the mechanical stop elements 152a and 152b in the example of FIGS. 1 through 6), but instead includes elements that provide, for example, visual feedback (in place of or in addition to tactile feedback).

FIG. 7 depicts an isometric view of an example apparatus having fiducial marks, which may serve to provide such visual feedback, according to the present disclosure. FIGS. 8-10 depict isometric broken views of the apparatus of FIG. 7 in three different actuation states.

As can be seen in FIG. 7, the apparatus 700 is similar in appearance to the apparatus 100, including, for example, an actuation mechanism 712, an elongate tubular structure 702, and a therapeutic device interface 708. In fact, for the purposes of discussion, it can be assumed that the apparatus 700 includes similar components and provides similar functionality to the apparatus 100, with the potential exception that the apparatus 700 may not include the mechanical stop elements 152a and 152b. Instead, or in addition thereto, the apparatus 700 includes fiducial marks 748, each of which corresponds to a different one of the first predetermined location, second predetermined location, and third predetermined location of the second portion/slider relative to the first portion/handle. In the depicted example, there are actually two sets of fiducial marks 748 that are, in effect, identical to each other—this accommodates more flexibility in how the apparatus 700 may be held without potentially completely obscuring one or more fiducial marks, but such redundant sets of fiducial marks are not necessarily required.

Also visible are reference features 750a and 750b, which are provided by the opposing end surfaces of the external portion of the slider 718. When the reference feature 750a, for example, lines up with any one of the three fiducial marks 748a, 748b, or 748c furthest from the elongate tubular structure 702, this indicates to the user that the slider 718 is in a corresponding one of the first predetermined location, second predetermined location, and third predetermined location relative to the first portion/handle 720. Similarly, when the reference feature 750b lines up with any one of the three fiducial marks 748a, 748b, or 748c closest to the elongate tubular structure 702, this indicates to the user that the slider 718 is in a corresponding one of the first predetermined location, second predetermined location, and third predetermined location relative to the first portion/handle 720.

It will be noted that while the reference features 750 in the apparatus 700 are provided by features of components that serve another purpose (the end surfaces of the external portion of the slider 718), other implementations may include a reference feature or features 750 that serve no other purpose except to act as reference marks, e.g., the side of the slider 718 may be imprinted or embossed with a triangle, arrow, or other reference feature. In some implementations, the positioning of the reference feature(s) and fiducial mark(s) may be reversed, e.g., with the fiducial marks on the moving element of the actuation mechanism 712 and the reference feature(s) on the stationary portion of the actuation mechanism 712.

It will also be noted that, for example, a combination of fiducial marks/reference features and mechanical stop features may be used in some implementations. For example, instead of fiducial marks 748a and 748c, the apparatus 700 may instead rely on a tactile mechanism, e.g., bottoming out of the slider 718 relative to the handle 720, to provide feedback to the user when the slider 718 is in the first or third predetermined locations relative to the handle 720. It will also be noted that the fiducial marks and/or reference features 748 and/or 750 may, in some cases, represent a small range of positions, e.g., within a zone of one or several millimeters in length, that are considered to all be, for example, potentially acceptable second predetermined locations. Other implementations, such as the apparatus 100 discussed earlier, may also be designed to allow for a small ranges of positions to serve as the first, second, and/or third predetermined locations, e.g., by extending the notch/element 152b to allow for some amount of sliding between it and the bump or protrusion on the beam spring/element 152a when the bump or protrusion is interfaced with the notch/element 152b.

Figure 11:
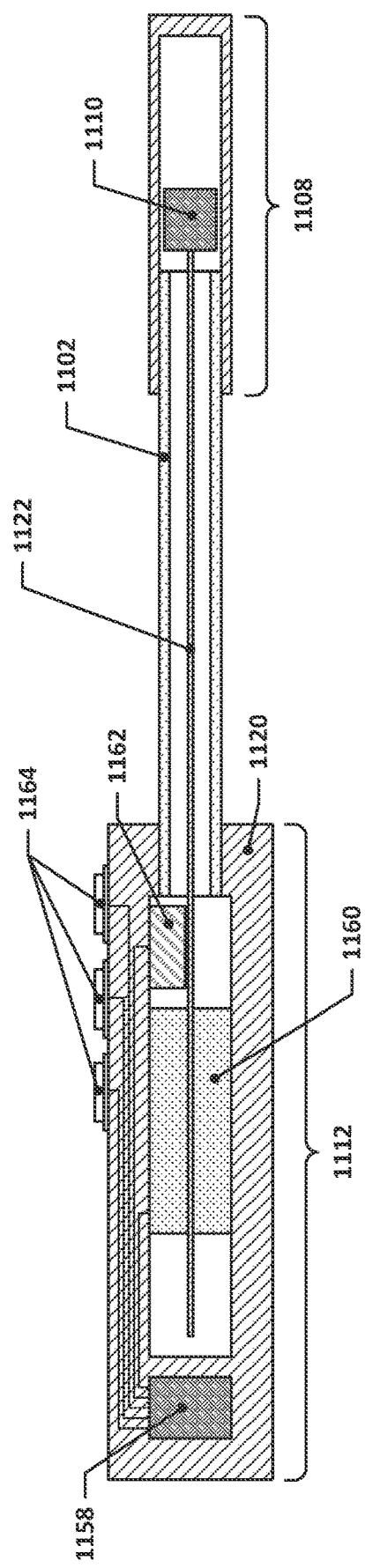
FIG. 11 depicts a schematic of another example apparatus according to the present disclosure.

FIG. 11 depicts another example apparatus. The apparatus 1100 of FIG. 11 is electromechanical in nature, and features an actuation mechanism 1112 with a controller 1158, an actuator 1160, and a position sensor 1162. The apparatus 1100 also includes an actuation member 1122, an elongate tubular structure 1102, a therapeutic device interface 1108, and a magnet 1110 positioned within the therapeutic device interface 1108 and connected with the actuation member 1122. The actuation member 1122 may be connected with the actuator 1160 such that the actuator 1160 can, responsive to inputs provided by the controller 1158, cause the actuation member 1122—and thus the magnet 1110—to move relative to the elongate tubular structure 1102. The controller 1158 may, for example, include one or more processors and memory storing computer-executable instructions for controlling the one or more processors to, for example, receive inputs from controls 1164 that indicate user interactions with the apparatus 1100 to cause the apparatus 1100 to enter one of at least three different states, each state associated with a different amount of extension or retraction of the actuation member 1122 and associated movement of the magnet 1110. The position sensor 1162 may provide input to the controller 1158 that indicates the amount of extension or retraction, or the position, of the actuation member 1122 relative to the actuation mechanism 1112. Thus, the controller can, using the feedback provided by the position sensor 1162, precisely control the actuator 1160 to cause the actuation member 1122 to move between various positions corresponding with, for example, the first predetermined location, second predetermined location, and third predetermined location relative to the actuation mechanism 1112. In some such implementations, the actuation member 1122 may have an end that interfaces with the actuator 1160 that may server as the "second portion" of the actuation mechanism 1112.

It will be further understood that a variety of different types of position sensor or sensors may be used, including, for example, multiple optical or physical switches that are each activated and/or deactivated when the actuation member 1122 is in particular corresponding predetermined locations, optical linear indexer sensors, linear displacement sensors, etc. It will also be understood that the controller, in some cases, may simply be a circuit or circuits that provide control functionality that causes the actuator 1160 to move the actuation member 1122 between the various predetermined locations responsive to various user inputs, e.g., provided via the controls 1164.

The above-discussed examples are shown as being configured for use with an annular therapeutic device that may be magnetically mated to the distal end of a therapeutic device interface. Such configurations may generally be suitable for placing such therapeutic devices on tissue walls that are generally transverse to the center axis of the therapeutic device interface. In such apparatuses, the centerline of the therapeutic device interface, e.g., the axis along which the magnet translates during actuation, may pass through the therapeutic device when the therapeutic device is magnetically mated to the therapeutic device interface.

With some modification, such apparatuses may also be used in situations where a therapeutic device is to be placed onto tissue that is generally parallel to the center axis of the therapeutic device interface. In such apparatuses, the therapeutic device may be positioned, when magnetically mated to the therapeutic device interface, such that it is offset from, and does not intersect with, the centerline of the therapeutic device interface and/or the elongate tubular structure. Such configurations may generally magnetically mate the therapeutic device to a side of the therapeutic device interface, thereby allowing the therapeutic device to be placed against tissue walls that are generally parallel to the centerline of the therapeutic device interface.

FIG. 12 depicts a top, non-planar section view of an example apparatus according to the present disclosure and in a first state. FIG. 13 depicts a side section view of the example apparatus of FIG. 12. FIG. 14 depicts a top, non-planar section view of the example apparatus of FIG. 12 but in a second state. FIG. 15 depicts a side section view of the example apparatus of FIG. 14. FIG. 16 depicts a top, non-planar section view of the example apparatus of FIG. 12 but in a third state. FIG. 17 depicts a side section view of the example apparatus of FIG. 16.

The apparatus 1200 of FIG. 12 is similar in design to the apparatus 100. In the interest of brevity, the various components of the apparatus 1200 that are the same or similar to corresponding components in the apparatus 100 are called out with callout numbers that share the same last two digits, and the previous discussion of such elements with respect to the apparatus 100 may be considered to be applicable to corresponding elements in the apparatus 1200 unless otherwise indicated below.

The apparatus 1200 differs from the apparatus 100 most notably with respect to the therapeutic device interface 1208, which is arranged to house an annular or disk-shaped magnet 1210 such that the center axis of the magnet 1210 is perpendicular to the axis of translation of the magnet 1210 responsive to movement of the actuation member 1222. This aligns the magnetic field generated by the magnet 1210 such that an annular therapeutic device may be magnetically clamped against the side of the therapeutic device interface, generally overlaying and aligning with the magnet 1210.

As can be seen, the therapeutic device interface 1208 may include one or more stop features 1246 that are defined by one or more stop surfaces 1244 that may, when a suitably sized therapeutic device is interfaced with the therapeutic device interface 1208, prevent the therapeutic device from moving along the side of the therapeutic device interface 1208 by a corresponding amount when the magnet 1210 is moved responsive to movement of the second portion from the first predetermined location relative to the first portion to the second predetermined location relative to the first portion.

For example, the stop surfaces 1244 may define an arcuate or near-arcuate surface or surfaces that inscribe a circular perimeter that is slightly larger than an outer diameter of the therapeutic device such that the therapeutic device may be placed within the circular perimeter but is generally constrained from sliding radially by the stop surfaces 1244. This allows the magnet 1210 to be moved relative to the therapeutic device without having the therapeutic device move a similar amount (although the therapeutic device may still move slightly until it contacts the stop surfaces 1244).

FIG. 18 depicts an isometric view of the example apparatus of FIG. 12 with a therapeutic device mounted to the therapeutic device interface. FIG. 19 is a broken isometric view showing the apparatus of FIG. 18 with the therapeutic device lifted off of the therapeutic device interface. As can be seen from FIGS. 18 and 19, a therapeutic device 1232 may be mated to the therapeutic device interface 1208 as shown in FIG. 18; FIG. 19 depicts the same therapeutic device 1232 lifted off of the therapeutic device interface 1208. As can be seen, the stop surfaces 1244 in this example consist of two opposing co-radial arcuate surfaces that define a generally circular area sized somewhat larger than the depicted therapeutic device 1232.

FIG. 20 is an isometric view of a pair of therapeutic devices, a first therapeutic device 2032 and a second therapeutic device 2034, pulled away from each other at an angle. During operation, each of the first therapeutic device 2032 and the second therapeutic device 2034 may be inserted into a different anatomical passage or different portion of the same anatomical passage and placed proximate to each other with the tissue walls of the anatomical passage(s) sandwiched in between them. When properly placed, the therapeutic devices 2032 and 2034 may cooperate to gradually cause an anastomosis to form between the tissue walls of the anatomical passage(s). This is shown in more detail in FIGS. 21-28, which depict various stages of therapeutic device installation using apparatuses such as are disclosed herein.

In FIG. 21, two apparatuses 2100a and 2100b, each with a corresponding therapeutic device interface 2108a and 2108b, elongate tubular structure 2102a and 2102b, and actuation mechanism 2112a and 2112b, are magnetically mated with a first therapeutic device 2132 and a second therapeutic device 2134, respectively, and the therapeutic device interfaces 2108a and 2108b thereof then inserted into an anatomical passage or anatomical passages having tissue walls 2166a and 2166b. The apparatuses 2100a and 2100b are, for ease of reference, two instances of the apparatus 1200 discussed earlier and have actuation mechanisms that are similar to the actuation mechanisms 112 discussed with regard to apparatus 100. The anatomical passage(s) may, for example, be different portions of a digestive tract. For clarity, only a small portion of the anatomical passage or each anatomical passage is shown in FIGS. 21-28, and most of the elongate tubular structure 2102 is omitted as well to avoid undue clutter. The actuation mechanisms 2112a and 2112b may each be located outside of the subject's body such that an operator, e.g., a surgeon, may manipulate the actuation mechanisms 2112a and 2112b. The therapeutic device interfaces 2108a and 2108b may be maneuvered into position such that the therapeutic devices 2132 and 2134 are positioned on opposite sides of two adjacent tissue walls 2166a and 2166b. The actuation mechanisms 2112a and 2112b may, during such positioning (and during insertion of the therapeutic device interfaces 2108a and 2108b into the anatomical passages), have their movable second portions in the first predetermined locations relative to the first portions thereof to cause magnets 2110a and 2110b to be in positions that magnetically clamp the therapeutic devices 2132 and 2134 in place onto the therapeutic device interfaces 2108a and 2108b, respectively.

In FIG. 22, the apparatuses 2100a and 2100b have been further repositioned so as to cause the first therapeutic device 2132 to magnetically mate to the second therapeutic device 2134 with the tissue walls 2166a and 2166b sandwiched between them. Thus, the apparatus 2100a is magnetically mated to the first therapeutic device 2132, the first therapeutic device 2132 is magnetically mated to the second therapeutic device 2134, and the second therapeutic device 2134 is magnetically mated to the apparatus 2100b. Of these magnetic connections, the magnetic connections between the apparatuses 2100a and 2100b may be designed to be stronger than the magnetic connection between the first therapeutic device 2132 and the second therapeutic device 2134. This allows the apparatuses 2100a and 2100b to be used to pull the first therapeutic device 2132 and the second therapeutic device 2134 apart from one another, e.g., if repositioning of the therapeutic devices is needed, or if the first therapeutic device 2132 and the second therapeutic device 2134 need to be removed, e.g., to be replaced with a differently sized therapeutic device pair. By applying forces in opposite directions to the therapeutic device interfaces 2108a and 2108b, the first therapeutic device 2132 and the second therapeutic device 2134 may be separated from one another without, for example, unduly stressing the tissue walls 2166a and/or 2166b.

In FIG. 23, the actuation mechanism 2112b of the apparatus 2100b has been actuated so as to bring the second portion of the actuation mechanism 2112b into the second location relative to the first portion thereof, thereby causing the magnet 2110b to move into a position that still exerts some magnetic clamping force on the second therapeutic device 2134, but less than the magnetic clamping force that was exerted on the second therapeutic device 2134 by the magnet 2110b when the second portion of the apparatus 2100b was in the first predetermined location relative to the first portion of the actuation mechanism 2112b. The magnetic clamping force exerted on the second therapeutic device 2134 when the second portion of the actuation mechanism 2112b is in the second predetermined location relative to the first portion is also less than the magnetic clamping force that exists between the first therapeutic device 2132 and the second therapeutic device 2134 when properly installed.

Figure 24:
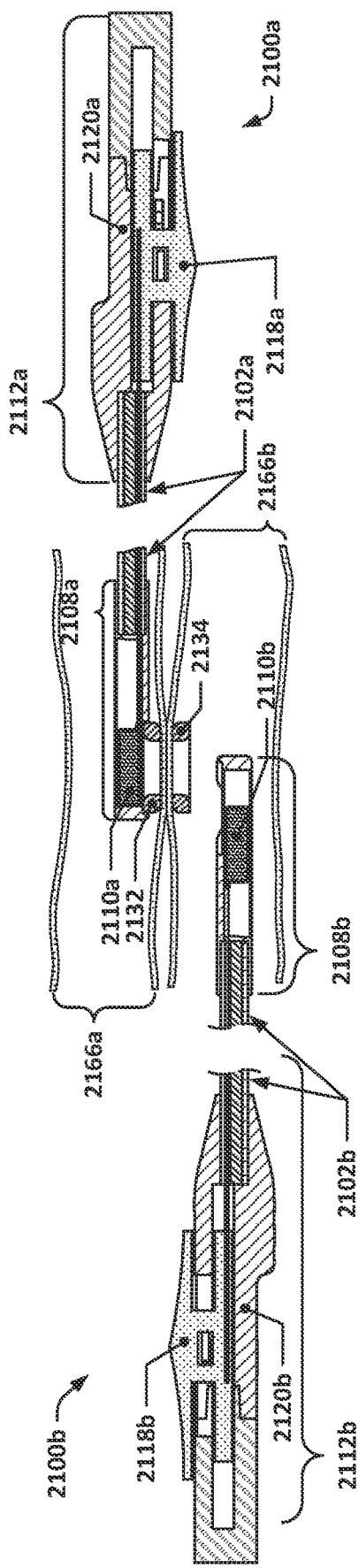

In FIG. 24, the apparatus 2100b has been manipulated (and the apparatus 2100a held in place) so as to cause the therapeutic device interface 2108b to be pulled away from the therapeutic device interface 2108a and the first therapeutic device 2132 with a force that exceeds the magnetic clamping force that exists between the second therapeutic device 2134 and the therapeutic device interface 2108b. This causes the second therapeutic device 2134 to remain clamped to the first therapeutic device 2132, which is, in turn, held in place by the apparatus 2100a, while the apparatus 2100b is pulled away and removed from the anatomical passage that it is in.

Figure 25:
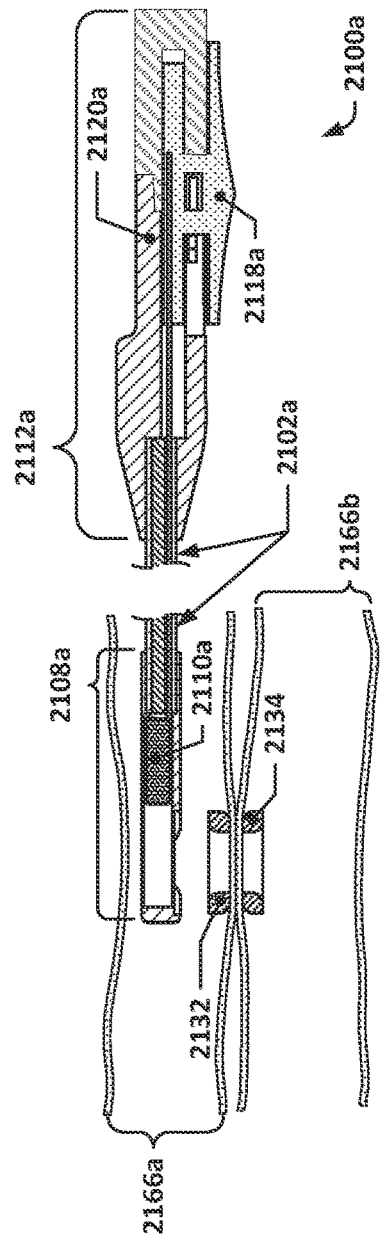

In FIG. 25, the actuation mechanism 2112a of the apparatus 2100a has been placed in a configuration in which the second portion thereof has been moved to the third predetermined location relative to the first portion thereof, thereby releasing the first therapeutic device 2132 from the therapeutic device interface 2108a. The first therapeutic device 2132 and the second therapeutic device 2134 thus remain clamped to one another as the apparatus 2100a is removed from the anatomical passage that it is in.

Figure 26:
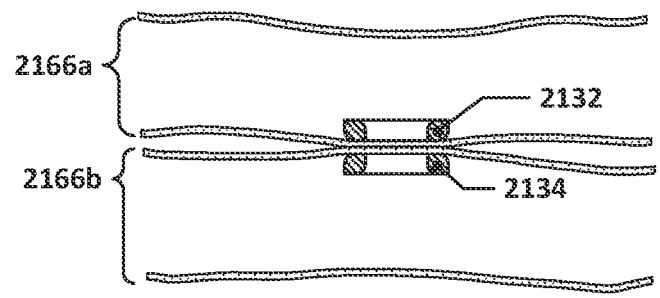
Figure 27:
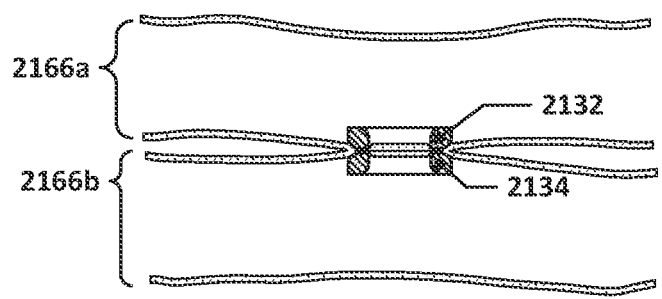
Figure 28:
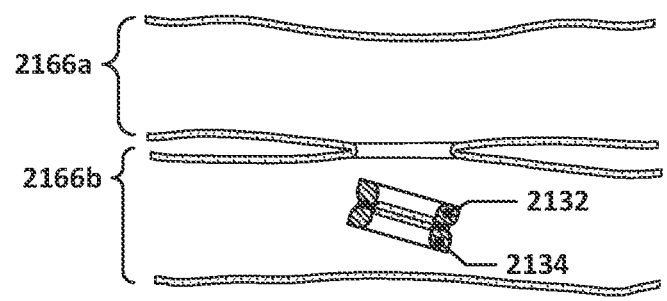

FIGS. 26 through 28 depict various stages of operation of the first therapeutic device 2132 and the second therapeutic device 2134. FIG. 26 depicts the first therapeutic device 2132 and the second therapeutic device 2134 as they would be shortly after installation. After some period of time, the tissue walls 2166a and 2166b that are compressed between the first therapeutic device 2132 and the second therapeutic device 2134 may compress, as shown in FIG. 27, due to the magnetic clamping force that exists between the first therapeutic device 2132 and the second therapeutic device 2134. At the same time, the tissue immediately adjacent to the outer perimeter of the clamped region of the tissue walls 2166a and 2166b starts to fuse together, as also shown in FIG. 27. Over time, the compressed portions of the tissue walls 2166a and 2166b will start to necrose due to the lack of blood flow therethrough resulting from the magnetic clamping. Finally, once sufficient necrosis has occurred, the necrotized, clamped portions of the tissue walls 2166a and 2166b may separate from the annular fused tissue wall region around the clamped-together first therapeutic device 2132 and second therapeutic device 2134, thereby allowing the clamped-together first therapeutic device 2132 and second therapeutic device 2134 and the necrotized tissue clamped therebetween to fall into one of the anatomical passages and be carried through the anatomical passage to a retrieval point (for example, for therapeutic devices that are installed in the digestive tract, the therapeutic devices may simply leave the subject through the normal process of defecation.

A similar process or technique may be used to place other types of therapeutic devices as well and may also be used with instruments such as the apparatus 100. It will also be understood that the various types of actuation mechanism discussed herein may also be used in the context of any of the apparatuses discussed herein.

As discussed earlier, the ability of the actuation mechanisms of the apparatuses discussed herein to have a movable element that may be moved between at least three predetermined locations allows such apparatuses to be used to support a therapeutic device such that the therapeutic device can be separated from another therapeutic device to which it is magnetically mated but also be switched to two other configurations—one in which the therapeutic device is completely released from the apparatus, and another where the therapeutic device is magnetically clamped to the apparatus but with a force that is tailored to the amount of magnetic clamping force that develops between the therapeutic device and a mating therapeutic device when the therapeutic devices are considered to be properly installed in a subject's anatomical passage(s).

What is claimed is:
1. An apparatus comprising:
   an elongate tubular structure having a first end and a second end;
   a therapeutic device interface located at the first end of the elongate tubular structure
   a magnet positioned within the therapeutic device interface;

an actuation mechanism connected with the second end of the elongate tubular structure, the actuation mechanism having a first portion that is fixed in space relative to the second end of the elongate tubular structure and a second portion that is movable relative to the second end of the elongate tubular structure; and an actuation member disposed within the elongate tubular structure, wherein:
the actuation member connects the magnet to the second portion of the actuation mechanism,
the actuation mechanism is configured to cause the second portion to be movable, responsive to one or more inputs, between at least a first predetermined location relative to the first portion, a second predetermined location relative to the first portion, and a third predetermined location relative to the first portion,
the second predetermined location relative to the first portion is in between the first predetermined location relative to the first portion and the third predetermined location relative to the first portion, and
the actuation member causes the magnet to move relative to the therapeutic device interface responsive to movement of the second portion of the actuation mechanism relative to the first portion of the actuation mechanism.

2. The apparatus of claim 1, wherein:
the therapeutic device interface is configured to support a corresponding first therapeutic device;
the first predetermined location relative to the first portion is selected such that when the second portion is in the first predetermined location relative to the first portion and the corresponding first therapeutic device is interfaced with the therapeutic device interface, the magnet is correspondingly positioned within the therapeutic device interface by the actuation member such that the corresponding first therapeutic device is magnetically mated to the therapeutic device interface by a first magnetic force generated between the magnet and the corresponding first therapeutic device;
the second predetermined location relative to the first portion is selected such that when the second portion is in the second predetermined location relative to the first portion and the corresponding first therapeutic device is interfaced with the therapeutic device interface, the magnet is correspondingly positioned within the therapeutic device interface by the actuation member such that the corresponding first therapeutic device is magnetically mated to the therapeutic device interface by a second magnetic force generated between the magnet and the corresponding first therapeutic device; and
the first magnetic force is greater than the second magnetic force.

3. The apparatus of claim 2, wherein the third predetermined location relative to the first portion is selected such that when the second portion is in the third predetermined location relative to the first portion and the corresponding first therapeutic device is interfaced with the therapeutic device interface, the magnet is correspondingly positioned within the therapeutic device interface by the actuation member such that the corresponding first therapeutic device is not magnetically mated to the therapeutic device interface by any magnetic force generated between the magnet and the corresponding first therapeutic device.

4. The apparatus of claim 2, wherein:
the first therapeutic device is configured to magnetically mate with a second therapeutic device such that a third magnetic force develops between the first therapeutic device and the second therapeutic device,
the third magnetic force is less than a first threshold force, and
the first magnetic force is greater than the first threshold force.

5. The apparatus of claim 4, wherein the first therapeutic device and the second therapeutic device are a matched pair of magnetic devices configured to generate an anastomosis when placed into a predetermined location in a biological organism with tissue sandwiched between them.

6. A kit comprising the apparatus of claim 5, the first therapeutic device, and the second therapeutic device.

7. The apparatus of claim 4, wherein the second magnetic force is less than the first threshold force.

8. The apparatus of claim 2, wherein the therapeutic device interface is connected with the first end of the elongate tubular structure and is configured to position the corresponding first therapeutic device such that a centerline of the elongate tubular structure passes through the corresponding first therapeutic device when the corresponding first therapeutic device is interfaced with the therapeutic device interface.

9. The apparatus of claim 2, wherein the therapeutic device interface is configured to position the corresponding first therapeutic device such that when the corresponding first therapeutic device is magnetically mated to the therapeutic device interface, the first therapeutic device is offset from, and does not intersect with, a centerline of the elongate tubular structure.

10. The apparatus of claim 9, wherein the therapeutic device interface:
has a body that includes an interior volume housing the magnet,
is sized to permit the magnet to slide along a first axis within the interior volume responsive to movement of the actuation member, and
includes one or more stop surfaces that define a stop feature that prevents the first therapeutic device from moving a corresponding amount relative to the therapeutic device interface when the first therapeutic device is magnetically mated with the therapeutic device interface and the magnet is moved responsive to movement of the second portion from the first predetermined location relative to the first portion to the second predetermined location relative to the first portion.

11. The apparatus of claim 1, wherein the first predetermined location relative to the first portion is selected so as to position the magnet further from the first end of the elongate tubular structure than the second location relative to the first portion.

12. The apparatus of claim 1, wherein:
the actuation mechanism includes at least one fiducial mark and one or more reference features,
the at least one fiducial mark and the one or more reference features are distributed between the first portion and the second portion such that the one or more reference features move relative to the at least one fiducial mark when the second portion is moved relative to the first portion, and
the at least one fiducial mark and the one or more reference features are positioned such that, for at least the second predetermined location relative to the first portion, at least one fiducial mark of the at least one fiducial mark aligns with at least one of the one or more reference features.

13. The apparatus of claim 1, wherein:

the actuation mechanism includes a plurality of mechanical biasing features, each mechanical biasing feature corresponds with a different one of the first predetermined location relative to the first portion, the second predetermined location relative to the first portion, and the third predetermined location relative to the first portion, the actuation mechanism is configured to cause the second portion to move relative to the first portion responsive to application of a first amount of force between the first portion and the second portion, and each mechanical biasing feature is configured to cause the first amount of force to increase when the second portion is in the corresponding one of the first predetermined location relative to the first portion, the second predetermined location relative to the first portion, and the third predetermined location relative to the first portion as compared locations at least immediately adjacent thereto.

14. The apparatus of claim 1, wherein:

the actuation mechanism includes a controller, an actuator, and one or more position sensors, and the controller is configured to cause the actuator to controllably move the second portion relative to the first portion to each of the first predetermined location relative to the first portion, the second predetermined location relative to the first portion, and the third predetermined location relative to the first portion responsive to one or more input signals and feedback from the one or more position sensors.

15. The apparatus of claim 1, wherein:

the apparatus is pre-configured to be used with a first therapeutic device, the first therapeutic device is configured to magnetically clamp to a second therapeutic device, the first predetermined location relative to the first portion is selected such that when the second portion is at the first predetermined location relative to the first portion and the first therapeutic device is located in a first relative position to the first end of the elongate tubular structure, the magnet is positioned such that the first therapeutic device is magnetically clamped to the apparatus with a clamping force that exceeds that generated between the first therapeutic device and the second therapeutic device when the first therapeutic device is clamped to the second therapeutic device, and the second predetermined location relative to the first portion is selected such that when the second portion is at the second predetermined location relative to the first portion and the first therapeutic device is located in the first relative position to the first end of the elongate tubular structure, the magnet is positioned such that the first therapeutic device is magnetically clamped to the apparatus with a clamping force that is less than that generated between the first therapeutic device and the second therapeutic device when the first therapeutic device is clamped to the second therapeutic device.

16. The apparatus of claim 1, wherein the elongate tubular structure is made of a flexible material.

17. The apparatus of claim 16, further comprising a malleable core that extends through the elongate tubular structure.

* * * * *